United States Patent
Vagman et al.

(10) Patent No.: US 9,582,870 B2
(45) Date of Patent: Feb. 28, 2017

(54) METHOD AND SYSTEM FOR ANALYZING PROCESS MONITORING DATA

(71) Applicant: HEXAGON METROLOGY (ISRAEL) LTD., Ramat Hasharon (IL)

(72) Inventors: Tal Vagman, Tel Aviv (IL); Jordi Edo Abella, Barcelona (ES)

(73) Assignee: HEXAGON METROLOGY (ISRAEL) LTD., Ramat Hasharon (IL)

( * ) Notice: Subject to any disclaimer, the term of this patent is extended or adjusted under 35 U.S.C. 154(b) by 0 days.

(21) Appl. No.: 14/634,544

(22) Filed: Feb. 27, 2015

(65) Prior Publication Data
US 2015/0248755 A1    Sep. 3, 2015

(30) Foreign Application Priority Data

Feb. 28, 2014    (EP) .................................... 14157229

(51) Int. Cl.
*G06T 7/00*    (2006.01)
*G01B 21/04*    (2006.01)
(Continued)

(52) U.S. Cl.
CPC .......... *G06T 7/0004* (2013.01); *G01B 21/047* (2013.01); *G01N 21/8803* (2013.01);
(Continued)

(58) Field of Classification Search
CPC .............. G01N 21/88; G01N 2223/645; G06T 2207/30168; B23Q 17/2409
(Continued)

(56) References Cited

U.S. PATENT DOCUMENTS

| 7,672,500 B2 | 3/2010 | Albeck et al. |
| 2004/0061778 A1* | 4/2004 | Yamane ................. G01N 21/89 348/86 |

(Continued)

FOREIGN PATENT DOCUMENTS

| DE | 195 44 240 A1 | 6/1996 |
| EP | 2 535 781 A1 | 12/2012 |

(Continued)

OTHER PUBLICATIONS

DE 19544240; as cited in the IDS dated Feb. 27, 2015 translation of reference provided.*

*Primary Examiner* — Bhavesh Mehta
*Assistant Examiner* — Narek Zohrabyan
(74) *Attorney, Agent, or Firm* — Maschoff Brennan

(57) ABSTRACT

Some embodiments of the invention include a method for capturing and analyzing monitoring data of a measuring system. In some embodiments, the measuring system may include one or more sensors and being adapted for a measuring operation of a series of identical objects the measuring operation comprising a multitude of measuring sequences, each measuring sequence comprising the measuring of values of features of an object of the series, the method comprising a multitude of monitoring operations, wherein each monitoring operation comprises capturing monitoring data during a measuring sequence, the monitoring data of each measuring sequence including at least one image comprising the measuring system and/or a measurement environment, characterized by selecting a subset of measuring sequences from the multitude of measuring sequences; and visualizing an image sequence comprising the images of the monitoring data of the measuring sequences of the subset.

14 Claims, 6 Drawing Sheets

(51) Int. Cl.
  *G05B 19/418* (2006.01)
  *G01N 21/88* (2006.01)
  *G06T 7/60* (2006.01)

(52) U.S. Cl.
  CPC ... *G01N 21/8851* (2013.01); *G05B 19/41875* (2013.01); *G06T 7/001* (2013.01); *G06T 7/60* (2013.01); *G01N 2201/06113* (2013.01); *G01N 2201/102* (2013.01); *G01N 2201/12* (2013.01); *G06T 2207/10016* (2013.01); *G06T 2207/30108* (2013.01); *Y02P 90/22* (2015.11)

(58) Field of Classification Search
  USPC .......................................... 382/241, 92, 141
  See application file for complete search history.

(56) References Cited

U.S. PATENT DOCUMENTS

| | | | | |
|---|---|---|---|---|
| 2007/0031024 A1* | 2/2007 | Albeck | ............ | G05B 19/41875 382/141 |
| 2007/0280501 A1* | 12/2007 | Walton | ............... | G01N 21/8806 382/100 |
| 2010/0215246 A1* | 8/2010 | Albeck | ............ | G05B 19/41875 382/141 |

FOREIGN PATENT DOCUMENTS

| | | |
|---|---|---|
| JP | H10-143237 A | 5/1998 |
| WO | 2005/124317 A2 | 12/2005 |
| WO | 2014029622 A1 | 2/2014 |

\* cited by examiner

METHOD AND SYSTEM FOR ANALYZING PROCESS MONITORING DATA

FIELD

The present invention pertains to the field of quality assurance for production processes. More specifically, the present invention relates to a system and a method for supervising and analyzing the monitoring of the output of a production process. This includes interpreting large data sets of basically identical measurement scenes collected over hours and days, visualizing monitoring data and trends throughout a shift using e.g. split screen and colour mapping for tool equalization and maintenance, identifying systematic errors, patterns and trends.

BACKGROUND

It is common practice during the industrial production of goods such as a car to measure features and properties of its different components. These measurements can be carried out in special measurement cells by means of either contact or non contact measuring gauges, for example based on laser or photogrammetric principles. Such a procedure, for instance, is disclosed in DE 195 44 240 A1.

U.S. Pat. No. 7,672,500 discloses a method for monitoring and visualizing the output of a production process, whose output materials or objects are inspected by one or more inspection units. The inspection units scan or otherwise inspect each of a series of objects or material being produced by a production process and an image is generated representing each of the inspected objects, wherein differences between the objects and information on the entire process can be visually coded.

The purpose of such methods is to determine possible errors of the measured object after production. Disadvantageously though, in the measurement process, there can occur various additional errors, that prevent or complicate the determination of the errors of the object. This is especially the case if a high precision detection of errors is needed.

On the one hand, errors can occur in the positioning of the object during the measurement, and on the other hand, further errors can occur in the measurement of every single sensor that is used for measuring the object.

From the European patent application with the application number 12425140.6 a method and device for minimizing errors in the positioning of the measured object are known. The solution disclosed therein utilizes a reference positioning system (RPS) for placing and aligning objects, for instance a car body, on a support. However, the disclosed solution does not consider sensor-inherent errors.

The method disclosed in the European patent application with the application number 13005240.0 allows the compilation of spatial measuring data from various sources about a single object into a single output file. According to this document, spatial measuring data can be processed to transform and integrate the data into a common reference system to be able to compare the measuring data with CAD data and to display the results in a unified way.

SUMMARY

In some embodiments, a report is outputted per every measurement cycle. Each report has to be reviewed and analyzed separately and independently, and cannot be compared easily to other cycle reports. In particular, it cannot be compared from a visual point of view to other cycles performed in the same day or shift. In-line errors are thus difficult to spot and be attended.

Some embodiments of the present invention provide an improved method and an improved system for identifying problems in the production process.

Some embodiments of the present invention include a method and system for determining possible errors of a measured object after production or of production process fluctuations.

Some embodiments of the present invention include a method and system for monitoring the process stability of a measuring system.

Some embodiments of the present invention include a method and system, wherein the amount of data and the time for computing, analyzing and reporting are reduced.

Some embodiments of the present invention include method and system for an improved monitoring and visualizing of the output of a production process.

Some embodiments of the present invention include a method and system that allows a user to easily recognize long-term patterns, such as trends in quality or iterations of systematic problems, in the production process.

Some embodiments include methods that are designed to be used for tool equalization and maintenance, problem solving, pin pointing time of trend shift from steady state and identifying error sources by identifying systematic errors, patterns or trends in the production process.

Some embodiments include methods that are provide end users with a high level analysis by watching an image sequence, i.e. a quick video clip. This video clip results from an automated or semi-automated generation of an image sequence out of existing measurement data (files or streams) that will allow unified multi-sensor results visualization. The method gives the user possibilities for interpreting large data sets of a multitude of identical objects collected over hours and days and quickly generates a lightweight high quality video clip in standard format which does not require a special program for viewing.

The method for capturing and analyzing monitoring data of a measuring system according to the present invention is adapted for monitoring the background of an object during a measurement of features of the object (i.e. for monitoring not the object itself but its surroundings) and allows visualization of a large dataset of measurement results and trends using e.g. split screen, colour mapping, on-screen statistics, highlights, summaries and comparisons, thus making the changes in measurement results over time more easily observable by a user. This can provide information about the produced objects and how the environment or background in which the objects are being produced is changing.

Thus, one aspect of the present invention pertains to a method for capturing and analyzing monitoring data of a measuring system, the measuring system comprising one or more sensors and being adapted for a measuring operation of a series of basically identical objects, the measuring operation comprising a multitude of measuring sequences, each measuring sequence comprising the measuring of values of features of an object of the series. This method comprises a multitude of monitoring operations, wherein each monitoring operation comprises capturing monitoring data during a measuring sequence, the monitoring data of each measuring sequence including at least one image comprising the measuring system and/or a measurement environment. According to the invention, this method furthermore comprises selecting a subset of measuring sequences from the multitude of measuring sequences, and visualizing an image sequence comprising the images of the monitoring data of the measuring sequences of the subset, wherein the order of the images in the image sequence is optimized for determining changes occurring in the measuring system and/or in the measurement environment and/or the production line including sourced materials.

The term "basically identical objects" in terms of this application is to be understood as meaning the same kind of objects or being small variants of the same product, in particular wherein the objects differ from each other—if at all—only within given production tolerances and/or by alterations from the planned design due to production errors. In particular, basically identical objects in terms of this application are more than 95% identical.

In one embodiment, the method according to the invention comprises subtracting data of the measured object from the monitoring data of the measuring sequences of the subset before visualizing the image sequence.

In another embodiment of the method, the visualization comprises colour mapping. In a further embodiment of the method, the image sequence provides the images in a non-chronological order.

In one embodiment of the method, the subset comprises no more than a tenth of the total number of measuring sequences of the same time period, in particular no more than a fiftieth.

In one embodiment of the method, the monitoring operations are performed only for the subset of the measuring sequences. In another embodiment, each monitoring operation comprises capturing an image at a pre-defined condition of the measuring system or at a pre-defined point in time of the measuring sequence.

In a further embodiment of the method, the measuring sequences of the subset are distributed evenly over the multitude of measuring sequences.

In another embodiment of the method according to the invention, for preventing artifacts, the subset of the measuring sequences are distributed unevenly over the multitude of measuring sequences. In particular, the distribution of monitoring operations is at least partially subject to a randomization.

In a particular embodiment, the monitoring data comprises temperature data of a surface of a part of the measuring system and/or of the measurement environment.

In a further embodiment of the method according to the invention, the visualization comprises a statistical analysis, particularly comprising a Fourier analysis for identifying periodical events.

The invention also pertains to a process monitoring system for capturing and long-term analyzing of monitoring data of a measuring system, the measuring system comprising one or more sensors and being adapted for a measuring operation of a series of same objects, the measuring operation comprising a multitude of same measuring sequences, each measuring sequence comprising the measuring of values of features of an object of the series. This monitoring system comprises at least one monitoring means adapted to perform a multitude of monitoring operations, wherein each monitoring operation comprises capturing monitoring data during a measuring sequence, the monitoring data including at least one image of the measuring system and of a measurement environment. According to the invention, the monitoring system comprises computing means adapted to select a subset of measuring sequences from the multitude of measuring sequences, and adapted to visualize an image sequence comprising the images of the monitoring data of the measuring sequences of the subset, wherein the order of the images in the image sequence is optimized for determining changes occurring in the measuring system and/or in the measurement environment.

In one embodiment of the process monitoring system according to the invention, the at least one monitoring means is a part of the measurement system and adapted to measure values of features of an object of the series.

In another embodiment of the process monitoring system, the at least one monitoring means is adapted to capture surface temperature data of a part of the measuring system and/or of the measurement environment.

In a further embodiment of the process monitoring system, at least two monitoring means adapted to capture at least two images at the same time from different positions, two images in different wavelengths, a stereoscopic image, and/or an image and a point cloud of the same surface.

In one embodiment, the computing means is adapted to subtract data of the measured object from the captured monitoring data.

In another embodiment, the computing means is adapted to analyze the monitoring data statistically. Particularly, the computing means is adapted to perform a Fourier analysis for identifying periodical events.

In another embodiment, the computing means is adapted to match monitoring data from various measurement systems and integrate them to a single view. Particularly the computing means is adapted to perform part matching and flush and gap analysis to determine match between key assembled parts before their actual assembly.

The invention also pertains to a computer programme product, comprising programme code which is stored on a machine-readable medium, or being embodied by an electromagnetic wave comprising a programme code segment, having computer-executable instructions for performing, in particular when run on a computing means of a process monitoring system according to the invention, at least the following steps of the method according to the invention:
 selecting a subset of measuring sequences from the multitude of measuring sequences; and
 visualizing an image sequence comprising the images of the monitoring data of the measuring sequences of the subset, wherein the order of the images in the image sequence is optimized for determining changes occurring in the measuring system and/or in the measurement environment.

Another aspect of the invention relates to a method for monitoring and visualizing the output of a production process. According to this aspect, such a method comprises a multitude of inspection processes of a set of basically identical objects, each object having one or more features, each inspection process comprising measuring and/or extrapolating one or more inspection values of at least one feature of an object of the set by means of at least one sensor system comprising at least one sensor. The method further comprises
 storing corresponding inspection and/or difference values from each inspection process together with meta data of the respective inspection process in a data storage device, the difference values being determined by comparing at least one of the inspection values against a corresponding stored nominal value, the meta data comprising an identifier of the respective object, inspection process and/or sensor system and/or a time of inspection; and
 generating a video output comprising a visual report template for sequentially presenting data of a multitude of the objects to a user, wherein for each object of the multitude the video output comprises a simultaneous presentation of at least two different views on representations of the object, visualized inspection and/or difference values, and meta data.

One embodiment of this method comprises selecting a subset of inspection processes from the multitude of inspection processes for presenting data of a multitude of objects corresponding to the subset, particularly wherein the subset comprises no more than a tenth of a total number of inspection processes of a given time period, in particular no more than a fiftieth. Optionally, the inspection processes of the subset are distributed evenly over the multitude of inspection processes, in particular wherein the data is presented in the video output corresponding to a chronological order of the inspection processes. Alternatively, for preventing artifacts, particularly for preventing aliasing effects, the inspection processes of the subset are distributed unevenly over the multitude of inspection processes, in particular wherein the distribution of inspection processes is at least partially subject to a randomization function.

In another embodiment of the method, a computing device is used to generate, based on the inspection and/or difference values, a model of each of the multitude of objects, particularly of each inspected object. Particularly, the models are three-dimensional models and/or are used as representations of the objects in the video output.

In a further embodiment of the method, a computing device is used to perform statistical analysis on corresponding inspection and/or difference values associated with corresponding points on each of the inspected objects to derive a statistical analysis based data set, particularly wherein the appearance of the visual report template is based on the data set.

The second aspect of the invention also relates to a process monitoring system for capturing and long-term analyzing inspection data of the output of a production process. It comprises a sensor system having one or more sensors and being adapted for performing a multitude of inspection processes on a set of basically identical objects, each inspection process comprising measuring and/or extrapolating one or more inspection values of at least one feature of an object of the set, and a data storage device adapted to storing corresponding inspection and/or difference values from each inspection process together with meta data of the respective inspection process, the difference values being determined by comparing at least one of the inspection values against a corresponding stored nominal value; the meta data comprising an identifier of the respective object, inspection process and/or sensor system and/or a time of inspection.

According to the invention, the process monitoring system comprises computing means adapted to generate a video output comprising a visual report template for sequentially presenting data of a multitude of the objects to a user, wherein for each object of the multitude the video output comprises a simultaneous presentation of at least two different views on representations of the object, visualized inspection and/or difference values, and meta data.

The second aspect of the invention also relates to a computer programme product, comprising programme code which is stored on a machine-readable medium, or being embodied by an electromagnetic wave comprising a programme code segment, having computer-executable instructions for performing, in particular when run on a computing means of the process monitoring system according, at least the following step of the method for monitoring and visualizing the output of a production process: Generate a video output comprising a visual report template for sequentially presenting data of a multitude of the objects to a user, wherein for each object of the multitude the video output comprises a simultaneous presentation of at least two different views on representations of the object, visualized inspection and/or difference values, and meta data.

BRIEF DESCRIPTION OF THE FIGURES

The invention in the following will be described in detail by referring to exemplary embodiments that are accompanied by figures, in which.

DETAILED DESCRIPTION

Figure 1:
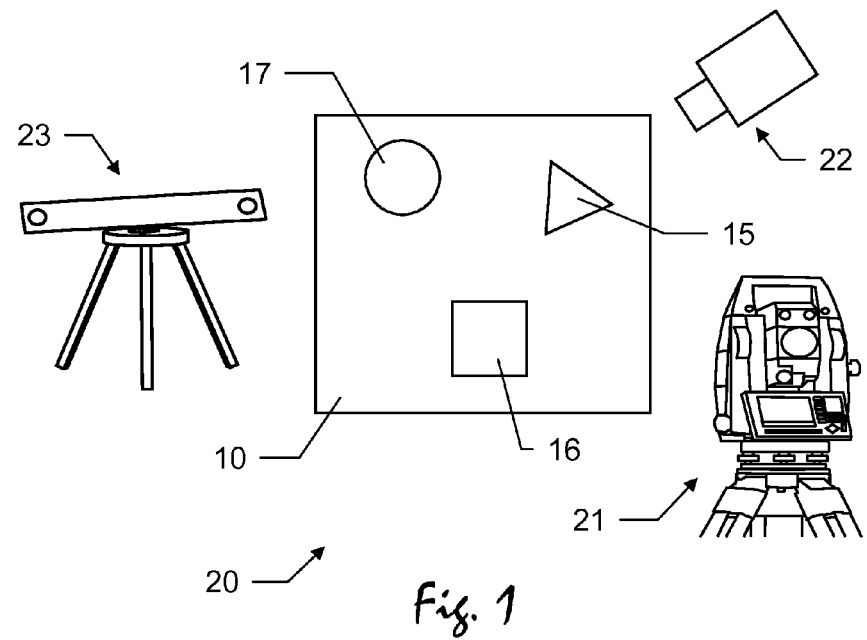
FIG. 1 shows an exemplary measuring system for measuring the output of a production process, measuring features of an object.

FIG. 1 shows an abstract example of a measuring system 20 measuring a number of features 15,16,17 of an object 10 for the purpose of quality control. The shown exemplary embodiment of a measuring system 20 according to the invention is adapted to measure spatial data of the object 10, particularly after the production of the object 10. The depicted measuring system 20 comprises three different sensors 21,22,23, which are adapted for measuring values of the three different features 15,16,17 of the object 10.

Figure 2:
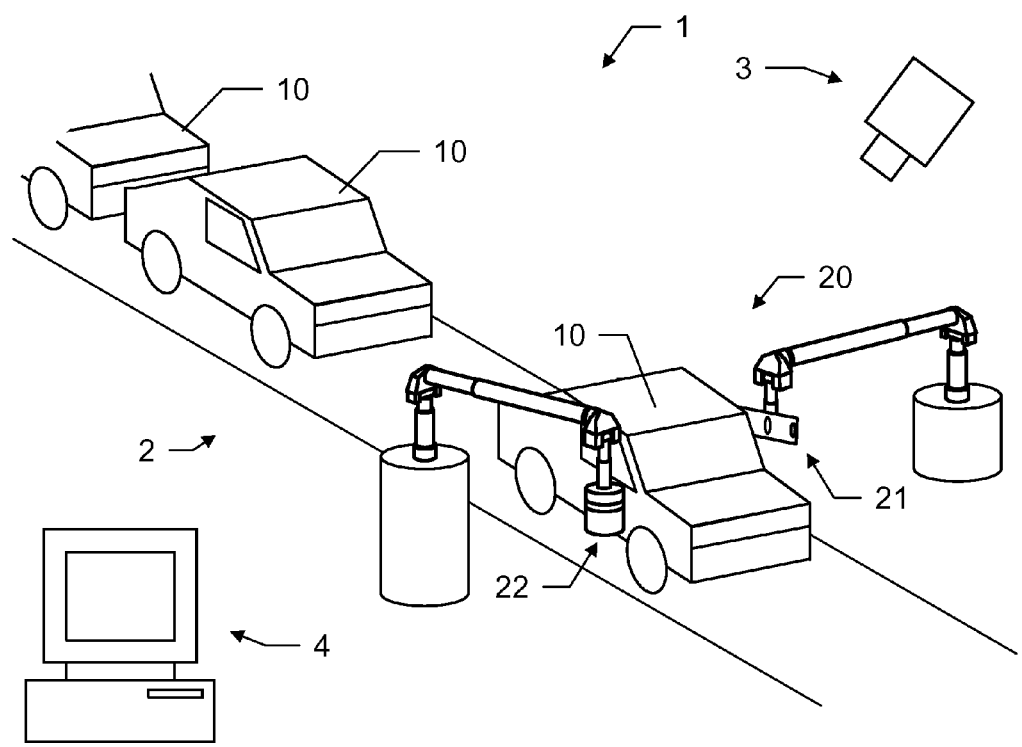
FIG. 2 shows an exemplary embodiment of a monitoring system according to the invention for capturing and analyzing monitoring data of a measuring system.

FIG. 2 shows an exemplary embodiment of a process monitoring system 1 for monitoring a measuring system 20 of a production line 2. The measuring system 20 measures a series of same objects after production—in this example these objects are cars 10.

The measuring system 20 comprises two different sensors 21,22 and is adapted to perform a measuring sequence for each car 10, wherein each measuring sequence comprises measuring values of features of the car 10 by means of the sensors 21,22.

The depicted exemplary measuring system 20 comprises two measuring robots having a first and a second sensor 21,22. The first sensor 21 is a white light scanner (WLS) and the second sensor 22 is a laser scanner. The WLS measures the outside surface of the car 10. The laser scanner measures (in parallel to the WLS) only edges of the car 10 for flush and gap information.

The process monitoring system 1 comprises a monitoring means 3 in form of a camera adapted to take images of the measuring system 20 during a measuring sequence. As known from prior art, the images can be provided to a user in real time or—for a short-term analysis—as a video clip, for instance after the end of each shift or as defined by the user.

The process monitoring system 1 can comprise a plurality of different monitoring means, for instance for synchronously taking images from different viewpoints. Optionally, also sensors of the measuring system 20 can be used as monitoring means of the process monitoring system 1.

The process monitoring system 1 furthermore comprises computing means 4, which according to the invention are adapted to visualize captured monitoring data of a small subset of the measuring sequences in a video clip of the images of the monitoring data of the subset of the measuring sequences.

The visualized subset comprises only a small part of the measuring sequences, in particular no more than a tenth of the total number of measuring sequences of the visualized period of time, especially no more than a fiftieth. Due to this, the frame rate of the film is low-frequent compared to the frequency of the measuring sequences. This allows the identification of long-term changes of the measurement system which are only visible at a low frequency.

Preferably, the computing means 4 are adapted to subtract data of the measured object from the captured monitoring data. This allows the user to focus on the changes in the background of the object, i.e. the measuring system and the measurement environment.

Together, the subtraction of the object data and the use of a small subset significantly reduce the amount of data that needs to be stored for this long-term analysis.

Figure 3:
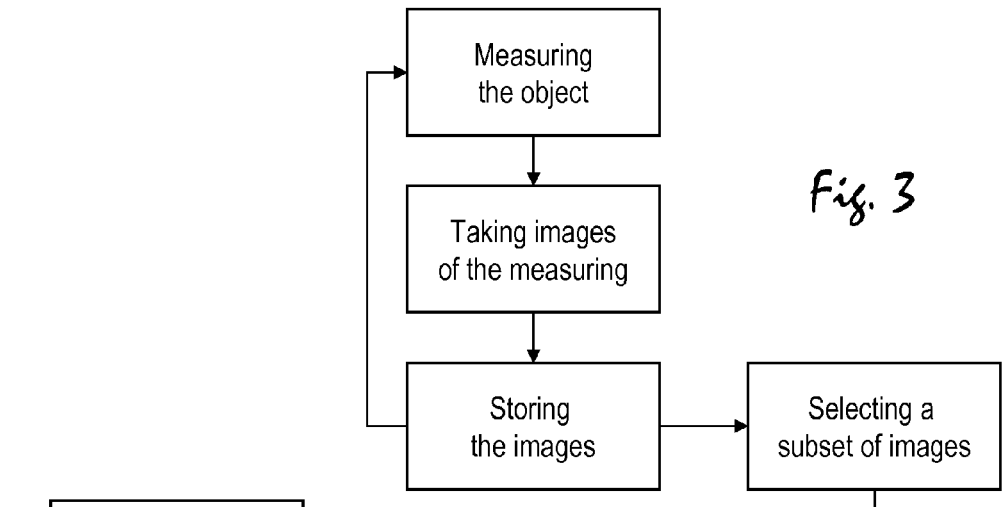
FIG. 3 illustrates a first exemplary embodiment of a method for capturing and analyzing monitoring data of a measuring system according to the invention.

FIG. 3 is a flow-chart illustrating a first exemplary embodiment of a method for capturing and analyzing monitoring data of a measuring system according to the invention.

The method comprises a measuring of an object of a series of identical objects, for instance after the production of these objects. During the measuring of the object, a monitoring system takes images of the measuring sequence, i.e. of the measuring system, the object and the background. These images and source data are stored on a central server. These steps are repeated for every object of the series of identical objects, the series being for instance the number of objects produced in a week, in a given number of shifts or in another period of time. Preferably, the data is made available for the computing application, so that it is accessible on demand.

From the stored images, images of a subset of measuring sequences are selected automatically. This selection may be pre-defined and/or subject to a randomization or to user defined settings on the fly (e.g. to analyze a specific occurrence).

From the selected subset of images an image sequence is created, for instance in form of a video clip. The order of the images of the image sequence is optimized for determining changes occurring in the measuring system and/or the measurement environment. This means that the images are not necessarily in a chronological order or in the order of the objects' serial numbers. Preferably, also the subset is selected in order to allow an optimal determining of changes occurring in the course of the measuring operation for the analyzed period of time, e.g. the shift or day. Finally, together with further data of the measuring sequences, meta data about the objects and production process, the image sequence is displayed to a user for allowing the user to determine changes occurring in the measuring system and/or in the measurement environment.

Figure 4:
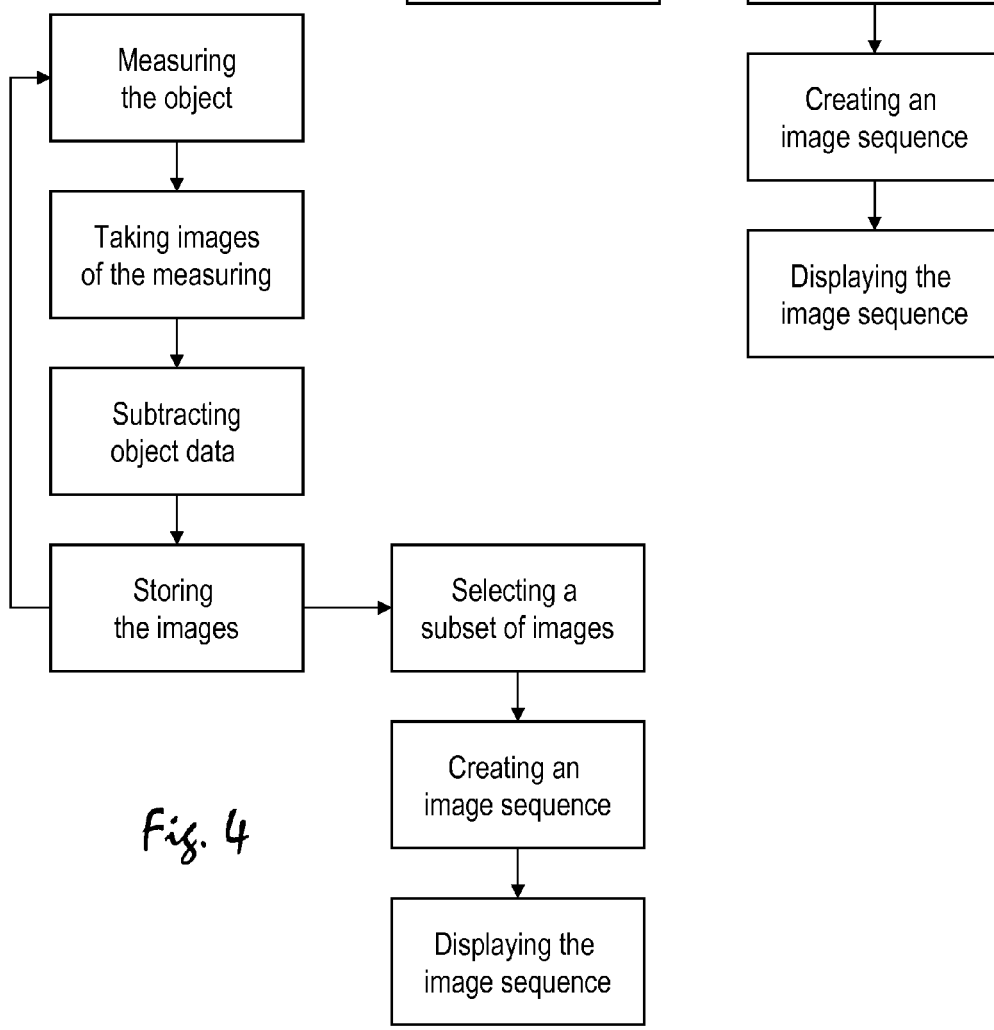
FIG. 4 illustrates a second exemplary embodiment of a method for capturing and analyzing monitoring data of a measuring system according to the invention.

FIG. 4 is a flow-chart illustrating a second exemplary embodiment of a method for capturing and analyzing monitoring data of a measuring system according to the invention. Additionally to the steps described above for FIG. 3, the method depicted in FIG. 4 comprises the step of subtracting object data from the images. This does not only reduce the size of the single image files but also helps the user to concentrate on the data of the measuring system and of the background influences.

In an alternative embodiment of the method, a subset of measuring sequences is selected before the beginning of the measurement process and images are taken only of the measuring sequences of this subset. Then, all stored images are used for creating the image sequence representing the subset of measuring sequences.

Figure 5A:
FIGS. 5a-b illustrate two exemplary subsets of measuring sequences, captured monitoring data of which being used for the generation of an image sequence.
Figure 5B:

FIGS. 5a and 5b show a number of consecutive measuring sequences (represented by the elevations), each with an exemplary subset of measuring sequences (represented by the black elevations), captured monitoring data of which being used for the generation of an image sequence.

In FIG. 5a the subset is distributed evenly over the multitude of measuring sequences, comprising every tenth measuring sequence. An even distribution facilitates an in-line trend analysis when visualizing large data set measurements along a timeline, e.g. when arranging the images in the image sequence in a chronological order.

In FIG. 5b the subset is distributed unevenly over the multitude of measuring sequences. This uneven distribution prevents the formation of artifacts in the image sequence. In particular, this pertains to aliasing effects, which can occur due to an unplanned and unforeseeable relationship between a certain constant measuring frequency (as shown in FIG. 5a) and the frequency of a periodic occurrence in the measured images. This periodic occurrence could then be falsely interpreted or overlooked.

The uneven distribution can have a pre-defined pattern, or be subject to a randomization function. Also, a partial randomization can be used, i.e. a combination of a pre-defined pattern and a randomization.

Figure 6:
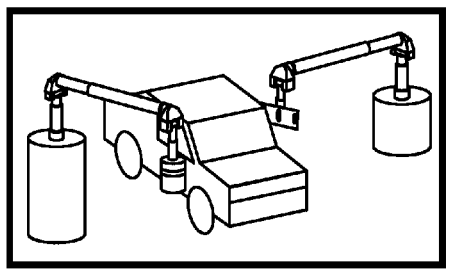
FIG. 6 shows an image of a measuring system as captured by the monitoring means for use in an image sequence.

FIG. 6 shows an image taken by a monitoring means of the measuring system during a measuring operation. The image comprises the sensors of the measuring system, the measured object and the measuring background. The background comprises all other objects and surfaces, such as the measuring robots.

Figure 7:
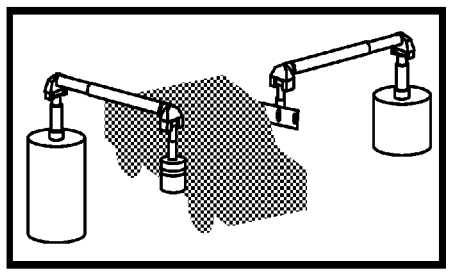
FIG. 7 shows the image of FIG. 4 after subtraction of the object data.

FIG. 7 shows the image of FIG. 6, from which the data of the measured objects has been subtracted, i.e. the object itself is not displayed in the image. For this subtraction, the object is recognized in the image and the data relating to the object is cut out. Advantageously, this reduces the size of the image files and also helps the user to concentrate on the data from the measuring system and the background when watching the image sequence.

Figure 10:
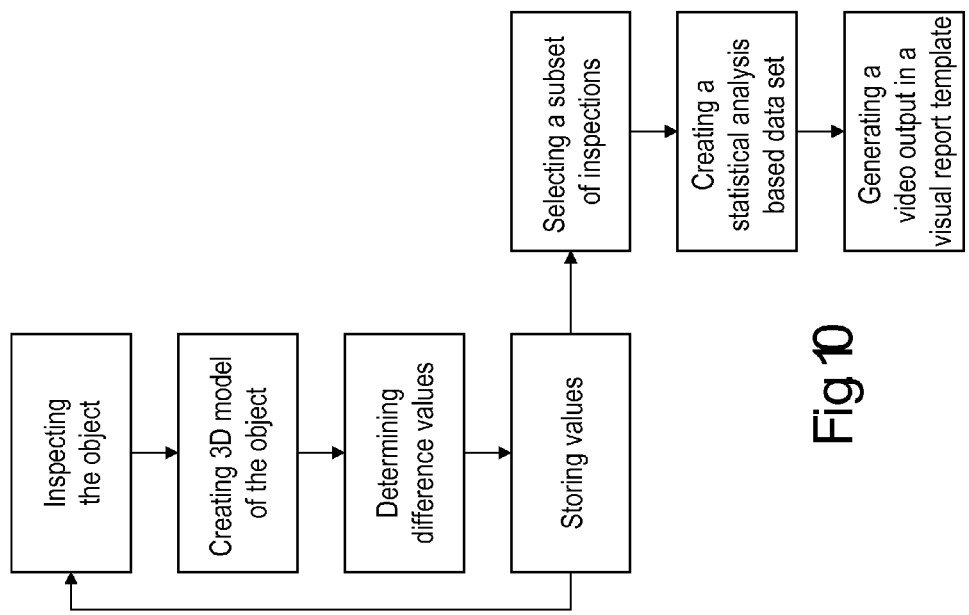
FIG. 10 illustrates an exemplary embodiment of a method for visualizing the output of a production process in a video sequence.
Figure 11:
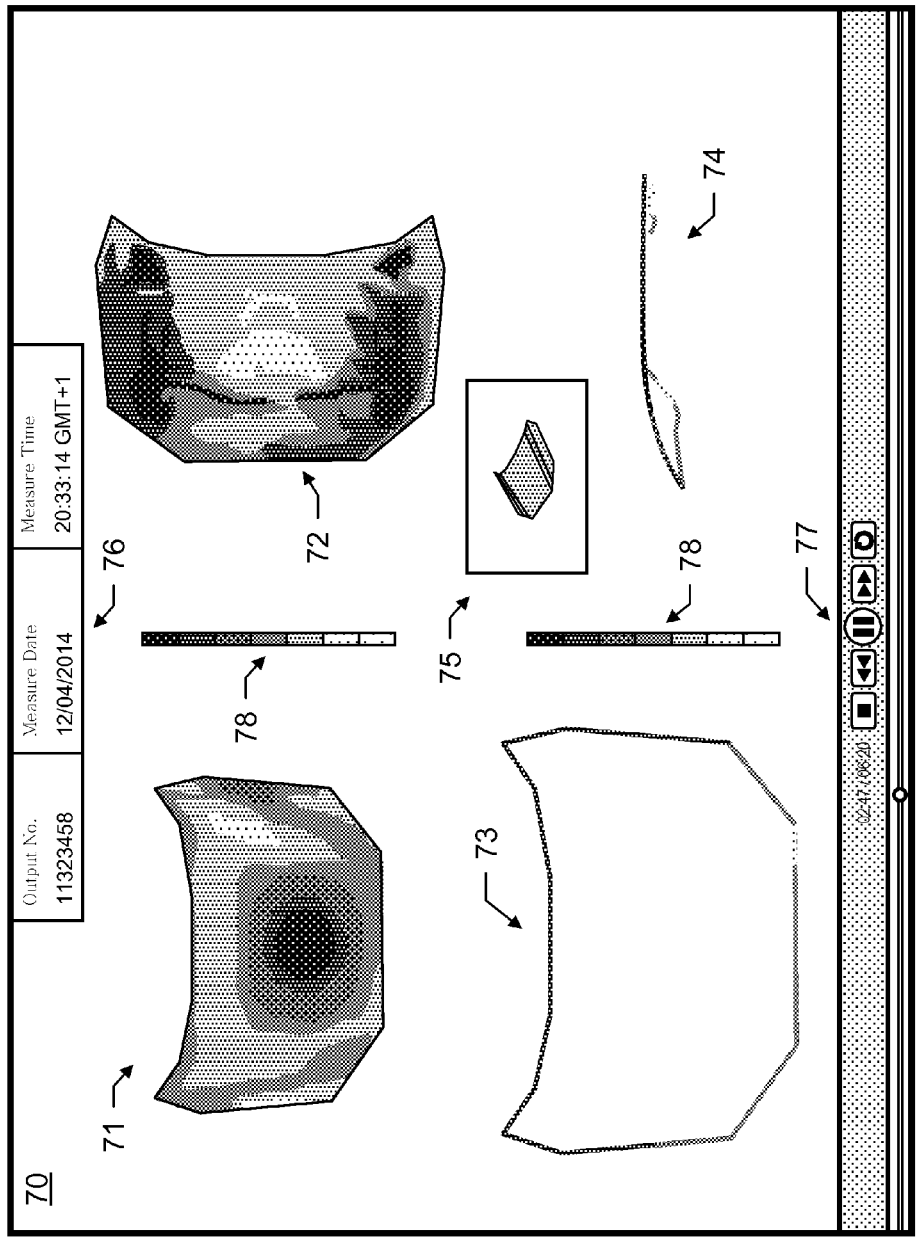
FIG. 11 shows a freeze image of a video output as displayed on a computer screen.
Figure 12:
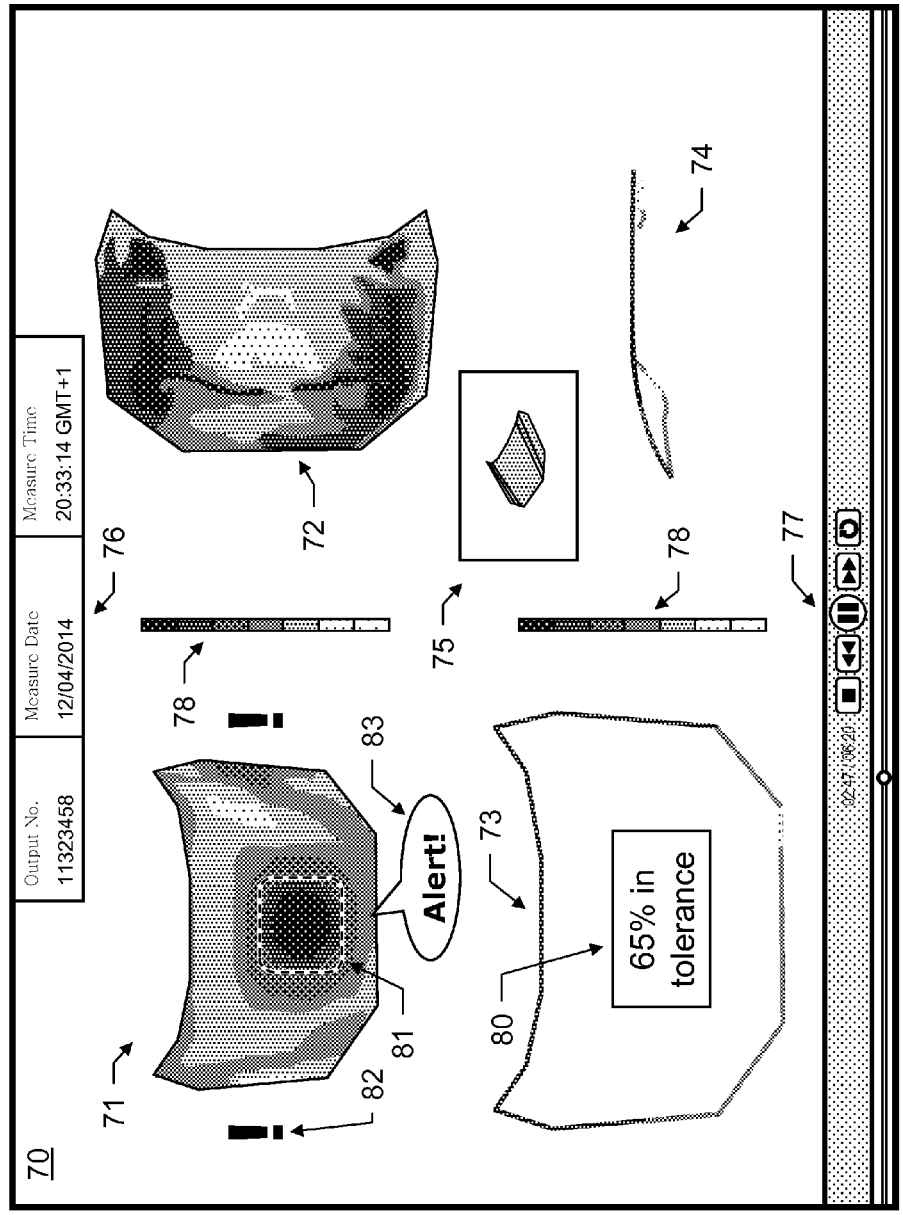
FIG. 12 shows the freeze image of FIG. 11 with additional statistical information, markings, and highlighting of detected issues.

Alternatively, if the background as well as the measured object is of interest, instead of subtracting data, measurement data of the objects as described with respect to FIGS. 10 to 12 can be added.

Figure 8:
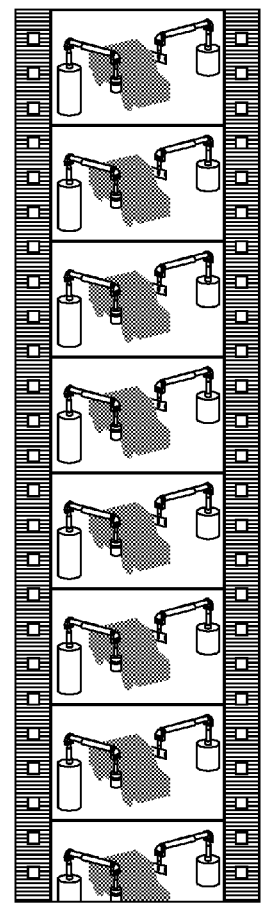
FIG. 8 shows a video clip as an image sequence comprising a multitude of images of the same measuring system.

FIG. 8 illustrates an image sequence in form of a video clip. As described for FIG. 7, object data has been subtracted from each image of the image sequence.

For generating the image sequence, images of the measurements of hundreds of identical objects being measured by a measuring system every hour, shift or day are used. These images are then compiled into an image sequence such as the depicted video clip where each frame is one of the images.

The video clip provides a quick and easy overview of an entire period of production—the measuring process of the produced objects is displayed in a clear and comparative format. An analysis based on the video thus neither consumes much time nor manpower. The video clip provides information about the production environment. Problems in the measuring process, in particular systematic errors, patterns and trends, can thus be easily identified, which can serve as a basis for tool equalization and maintenance.

The generation of the video clip is preferably based on a data server. It offers various triggering, selection and sorting functionalities that are not necessarily linked to a time sequence, i.e. the images of the image sequence do not have to be displayed in the chronological order of their creation. The image sequence is generated fully automatically without requiring any operator involvement. A serial number is associated with each image which can be referenced for further information.

The generation of the video clip may comprise integration with rules and process control and also trend detection. For instance, consecutive occurrences of a trending event will trigger the generation of a video clip with these parts included in the range.

The order of the images in the video clip is not necessarily chronological but rather optimized for determining changes occurring in the measuring system and in the measurement environment. Particularly a chronological order of the images allows an in-line trend analysis by visualizing large data set measurements along a timeline.

Software of the computing means may detect changes in the measurement system and environment data and highlight these for easier recognition by the user. Problematic instances can be automatically detected by the software and then marked the in video clip. A user can be enabled to add comments to those measurements. Additional visual analyses, such as graphical diagrams may be included in the clip as a summary.

Customized colour legends for each slide can be provided, including histograms and continuous or discrete modes.

Preferably, the user is enabled to sort and filter the images of the image sequence. Particularly, this includes sorting by time stamp and filtering options to a multi-results tree (as for instance included in the CoreView software) in order exclude certain results from the image sequence.

The visualization may also comprise at least one of the following:
- unifying subtracted monitoring data into single view data from multiple measurement systems or multiple measurement sequence on a similar object type;
- presenting integrated statistical info about the image and analysis such as histogram, average value, ranges, etc.;
- highlighting points in time and measured data which is of interest according to predefined rules; and
- matching data from different measurement system monitoring data to perform automatic or semi-automatic matching for predicting fit and finish quality.

Figure 9:
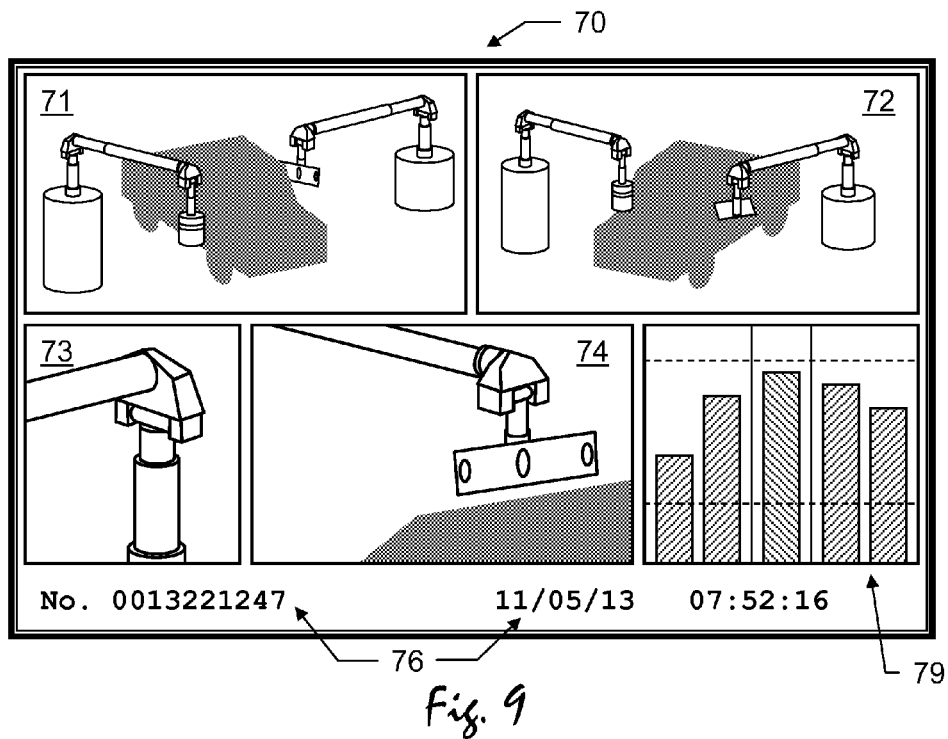
FIG. 9 shows a visualization of image sequences and further data on a screen.

FIG. 9 illustrates the visualization of data from a multitude of monitoring means in a visual report template 70 comprising a split screen. The split screen visualization provides a number of image sequences 71-74 each taken by a different monitoring means of the same subset of measuring sequences. It provides meta data 76 such as the date and time at which the presently shown images have been taken or e.g. the serial number of the measured object. Furthermore, measured data additionally can be presented in form of histograms or other diagrams 79.

The depicted visualization screen comprises two image sequences 71-72 of the measuring sequences showing the whole measuring system from two different viewpoints. It also comprises two image sequences 73-74 of the measuring sequences showing details of the measuring system, or the measurement environment, respectively. Here, two parts of the measurement robots are shown. Colour mapping in the images can be used to enhance the user's intuitive capabilities to quickly spot errors or problematic areas in the visualization (not shown here). For instance, dimensional deviations or changes in the spatial position of an object with respect to a set value, for instance CAD data of the measuring environment, or with respect to the preceding image can be illustrated by colours. Alternatively, absolute or relative surface temperatures can be illustrated this way.

Additionally, a histogram 79 is shown for visualizing further monitoring data captured during the respective measuring sequences. For instance, a temperature in the measurement environment (e.g. a robot or ambient temperature) for the presently visualized image of the image sequence and the temperatures for the preceding and following images might be displayed.

The user can select a range of measurements, e.g. the last 300 measurements of a specific part type, and a filtering and sorting method (e.g. filter or sort by time, serial number, deviation from set value, or measurement cycle state). The user can also choose the type of visualization. This includes the number of split screens, e.g. selecting the number of image sequences displayed simultaneously, and the kind of statistical summary.

The visualization may also comprise an automatic highlighting analysis, which, based on histogram analysis, automatically zooms into problematic areas or slows down the video clips at points of quality degradation.

Also, a statistical analysis can be done before the visualization, for instance comprising a Fourier analysis. The statistical analysis can also include average deviations, comparisons of start to finish, or ranges. The analysis e.g. can be used for determining frequencies of repeatedly occurring errors or changes, so that a cause for the errors or changes can be determined and disabled.

The visualization can also comprise a fully automated comparison of multiple cycle reports. Preferably, it grants a user the ability to filter or screen presented data from specific cycles, days, hours, lines or shifts.

The generation of the visualization files can be triggered by time (e.g. once a day or week), by quality (e.g. if too many errors are detected) or on demand by a user. Preferably, the visualization can be auto-distributed after generation of a visualization file to a defined audience of users, e.g. as an email attachment. Other auto-distribution options can e.g. comprise portal posting, saving the file to a network drive or sending push notifications to selected users, including to PC/Laptop, mobile and tablet devices.

FIG. 10 is a flow chart illustrating an exemplary embodiment of a method for visualizing the output of a production process in a video sequence. The method starts with a first inspection process on a first object which is one of a multitude of basically identical objects. "Basically identical" in this context is meant as either being the same product but possibly differing to a small extent from each other due to non-uniform production circumstances, or being small variants of the same product, in particular more than 95% identical. During the inspection, which is performed by a plurality of sensor units, inspection values of one or more features of interest are measured or extrapolated.

After the object has been inspected, a model of the object, particularly a three-dimensional model, is created by a computing unit based on the inspection values determined during the inspection process.

Then, by comparing one or more inspection values against corresponding stored values, at least one difference value is determined. The stored values particularly can be taken from CAD data and be stored in a data storage of the computing unit.

Then, the inspection and/or difference values of the first object are stored in a data storage together with meta data of the first inspection process. The meta data comprises for instance an identifier of the object, such as a serial number which has been read, e.g. by a barcode scanner or an RFID scanner, a sequential number of the inspection process or an identifier of the sensor system or systems performing the inspection process. Furthermore, the meta data may comprise date and time of the inspection or data of the surrounding, such as temperature, air pressure and humidity at the time of the inspection.

The above steps are repeated for all objects to be inspected. After all objects have been inspected and all values have been stored, from the multitude of inspection processes a subset is selected for visualisation. This selection can be performed as described for FIGS. 5a and 5b, i.e. be distributed evenly or unevenly over the multitude of inspection sequences. Again, the uneven distribution can have a pre-defined pattern, or be subject to a randomization function. Also, a partial randomization can be used, i.e. a combination of a pre-defined pattern and a randomization. Alternatively, the subset may also comprise all inspection processes.

The subset preferably is selected in such a way that long-term patterns in the production process, such as trends in quality or iterations of systematic problems, can be made visible to the user.

Then, a statistical analysis is performed on inspection values or difference values that are associated with corresponding points on the inspected objects of the selected subset. Based on this statistical analysis a data set is derived.

Based on the data set, a visual report template is defined or provided, which allows a plurality of views of the generated object models, and a video output is generated based on the visual report template. The video output comprises two or more simultaneous sequences of the object models of the subset, showing the same model from different views simultaneously, wherein inspection or difference values are made visible, e.g. by means of a colour map.

The video output is stored as a file and can be distributed to a plurality of users. The video output can then be watched by a user, e.g. on a computer screen, and long-term patterns can easily be recognized, to detect possible systematic errors in the production process or trends in the quality of the output.

FIG. 11 shows a possible result of the method of FIG. 10. It shows the video output (as a freeze image) generated by the method as it could be shown to a user, e.g. on a computer screen. The video output shows a visual report template 70 which comprises five different views 71-75 on a representation of an object that has been inspected as output of a production process. In this example, the inspected object is a bonnet for covering a car's engine. The video output also visualizes meta data 76 of the inspection corresponding to the shown object. In this example, the meta data comprises a serial number of the object ("Output No.") and the date and exact time of the inspection. The video can be controlled by the user by clicking on video control buttons 77, which allow stopping the video (e.g. for looking at one visual report template of special interest in detail), fast-forwarding, or rewinding the video. Optionally, the user can also choose the speed of the video, i.e. how long a visual report template 70 is visible until it is replaced by the next one.

In one of the five views the representation is an image 75 of the object taken during the inspection, the other four views 71-74 show three-dimensional models with difference values as a colour map. The first view 71 shows a colour-coded model of the bonnet from the top, the second 72 from the bottom. The third and fourth view 73,74 show the colour-coded edges of the bonnet. The different colours (in this figure represented by different shades) illustrate the difference of the measured (or extrapolated) value and a nominal value, for instance spatial deviations. For instance, large deviations to the one side might be represented by red, and those to the other side might be represented by violet, wherein areas with no or little deviations could be represented by green.

Legends 78 explaining the meaning of each colour in the respective view 71-74, e.g. a number range of the difference value, are also provided in this example.

The video output shows an objects sequence preferably in such a way that long-term patterns in the production process, such as trends in quality or iterations of systematic problems, become visible to the user.

FIG. 12 shows the same freeze image of the video output as FIG. 11, wherein further information has been added to the video output. In the third view 73 of the bonnet, a numerical value 80 shows a tolerance level value, and in the first view, different kinds of possible warning signs 81-83 are shown that may alert the user and draw his attention to an inspection or difference value exceeding a pre-defined threshold. The warning signs may comprise a highlighting 81 of the affected region, e.g. flashing; visual signs 82 appearing around the problematic model; and/or acoustic signals 83.

Additionally, background information, such as data about the used sensor system, can be displayed in the visual report template 70, e.g. as described above with respect to FIGS. 2 to 9.

Although the invention is illustrated above, partly with reference to some preferred embodiments, it must be understood that numerous modifications and combinations of different features of the embodiments can be made. All of these modifications lie within the scope of the appended claims.

What is claimed is:

1. A method for capturing and analyzing process monitoring data of a measuring system, the method comprising:
    performing with one or more sensors of the measuring system a measuring operation of a series of basically identical objects, the measuring operation comprising a multitude of measuring sequences, each measuring sequence comprising the measuring of values of features of an object of the series;
    performing a multitude of monitoring operations, wherein each monitoring operation comprises capturing monitoring data during a measuring sequence, the monitoring data of each measuring sequence including at least one image comprising the measuring system and/or a measurement environment;

selecting a subset of measuring sequences from the multitude of measuring sequences, the subset comprising no more than a tenth of a total number of measuring sequences of a given period of time; and visualizing an image sequence comprising the images of the monitoring data of the measuring sequences of the subset, wherein the order of the images in the image sequence is optimized for determining changes occurring in the measuring system and/or in the measurement environment, wherein:

the measuring sequences of the subset are distributed evenly over the multitude of measuring sequences, wherein the image sequence provides the images in a chronological order; or for preventing artefacts, particularly for preventing aliasing effects, the subset of the measuring sequences are distributed unevenly over the multitude of measuring sequences, wherein the distribution of monitoring operations is at least partially subject to a randomization function.

2. The method according to claim 1, further comprising:
subtracting data of the measured object from the monitoring data of the measuring sequences of the subset before visualizing the image sequence.

3. The method according to claim 1, further comprising:
generating a video output comprising a visual report template for sequentially presenting the images of the monitoring data of the measuring sequences of the subset to a user, wherein for each object of the subset the video output comprises a simultaneous presentation of at least two different image sequences.

4. The method according to claim 1, wherein:
the visualization comprises a statistical analysis, particularly comprising a Fourier analysis for identifying periodical events;
the visualization comprises colour mapping;
the visualization comprises a split screen showing at least two image scenes simultaneously; and/or
the image sequence provides the images in a non-chronological order.

5. The method according to claim 1, wherein:
the monitoring operations are performed only for the subset of the measuring sequences.

6. The method according to claim 1, wherein:
each monitoring operation comprises capturing an image at a pre-defined condition of the measuring system or at a pre-defined point in time of the measuring sequence.

7. The method according to claim 1, wherein:
the monitoring data comprises temperature data of a surface of a part of the measuring system and/or of the measurement environment and/or temperature data of the air.

8. The method according to claim 1, wherein:
the subset comprises no more than a fiftieth of a total number of measuring sequences of a given period of time.

9. A process monitoring system for capturing and long-term analyzing of monitoring data of a measuring system, wherein the measuring system is adapted for a measuring operation of a series of basically identical objects the measuring operation comprising a multitude of same measuring sequences, each measuring sequence comprising the measuring of values of features of an object of the series, wherein the monitoring system comprises:
at least one monitoring means adapted to perform a multitude of monitoring operations, wherein each monitoring operation comprises capturing monitoring data during a measuring sequence, the monitoring data including at least one image of the measuring system and of a measurement environment;
computing means configured to:
select a subset of measuring sequences from the multitude of measuring sequences, the subset comprising no more than a tenth of a total number of measuring sequences of a given period of time; and
visualize an image sequence comprising the images of the monitoring data of the measuring sequences of the subset, wherein the order of the images in the image sequence is optimized for determining changes occurring in the measuring system and/or in the measurement environment wherein the computing means are configured to select the subset so that:
the measuring sequences of the subset are distributed evenly over the multitude of measuring sequences, wherein the image sequence provides the images in a chronological order; or
the subset of the measuring sequences are distributed unevenly over the multitude of measuring sequences, wherein the distribution of monitoring operations is at least partially subject to a randomization function.

10. The process monitoring system according to claim 9, wherein at least one monitoring means is:
a part of the measurement system and adapted to measure values of features of an object of the series, and/or
adapted to capture surface temperature data of a part of the measuring system and/or of the measurement environment.

11. The process monitoring system according to claim 9, wherein at least two monitoring means adapted to capture at least:
two images at the same time from different positions,
two images in different wavelengths,
a stereoscopic image, and/or
an image and a point cloud of the same surface.

12. The process monitoring system according to claim 9, wherein the computing means is adapted to:
subtract data of the measured object from the captured monitoring data;
analyze the monitoring data statistically, wherein the computing means is adapted to perform a Fourier analysis for identifying periodical events; and/or
match monitoring data from various measurement systems and integrating them to a single view.

13. The process monitoring system according to claim 9, wherein the computing means is adapted to perform part matching and flush and gap analysis to determine match between key assembled parts before their actual assembly.

14. One or more non-transitory computer-readable media storing one or more programs that are configured, when executed, to cause one or more processors to execute the method of claim 1.

* * * * *